US00PP35478P2

(12) United States Plant Patent
Ammerlaan

(10) Patent No.: US PP35,478 P2
(45) Date of Patent: Nov. 14, 2023

(54) ***CRASSULA* PLANT NAMED 'OVWOODS05'**

(50) Latin Name: *Crassula arborescens*
Varietal Denomination: OVWOODS05

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/445,016

(22) Filed: Mar. 2, 2023

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct *Crassula* plant named 'OVWOODS05' which is characterized by the combination of a large plant size, large succulent foliage borne on long lateral branches, dark green and glaucous foliage, and the stability of all characteristics from generation to generation.

2 Drawing Sheets

Latin name of the genus and species: The Latin name of the genus and species of the novel variety disclosed herein is *Crassula arborescens*.

Variety denomination: The inventive variety of *Crassula* disclosed herein has been given the variety denomination 'OVWOODS05'.

BACKGROUND OF THE INVENTION

Parentage: 'OVWOODS05' originated as a naturally occurring, whole-plant mutation of *Crassula* 'OVCRAS03' (Community Plant Variety Rights grant number 46259), a variety developed and owned by the inventor. The inventor of 'OVWOODS05' is a commercial ornamental plant producer and regularly discovers mutations of *Crassula* at his greenhouse operation in Bleiswijk, The Netherlands. For said mutations which seem to exhibit commercial potential, cuttings are taken to produce trial plants which are subsequently grown for evaluation. The variety now called 'OVWOODS05' was initially discovered in December of 2017 as a whole-plant mutation of 'OVCRAS03' which exhibited a large size and dark green, glaucous foliage borne on long lateral branches. At the time of discovery, cuttings were taken and the resulting plants were evaluated at the inventor's greenhouse. After further evaluation it was determined that the candidate's foliage characteristics would prove favorable for commercial marketability. The new variety was given the breeder denomination 'OVWOODS05'.

Asexual Reproduction: The variety now called 'OVWOODS05' was first asexually propagated by stem cuttings in December of 2017 at a greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVWOODS05' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'OVWOODS05'. These characteristics in combination distinguish 'OVWOODS05' as a new and distinct *Crassula* cultivar:

1. *Crassula* 'OVWOODS05' exhibits a large plant size with a broad spreading to upright growth habit and an irregular broad obovate to near flattened globular profile; and
2. *Crassula* 'OVWOODS05' exhibits relatively large succulent foliage borne on long lateral branches; and
3. *Crassula* 'OVWOODS05' exhibits dark green, heavily glaucous foliage which is covered with greyed-green epicuticular wax.

BOTANICAL DESCRIPTION OF THE PLANT

Figure 1:
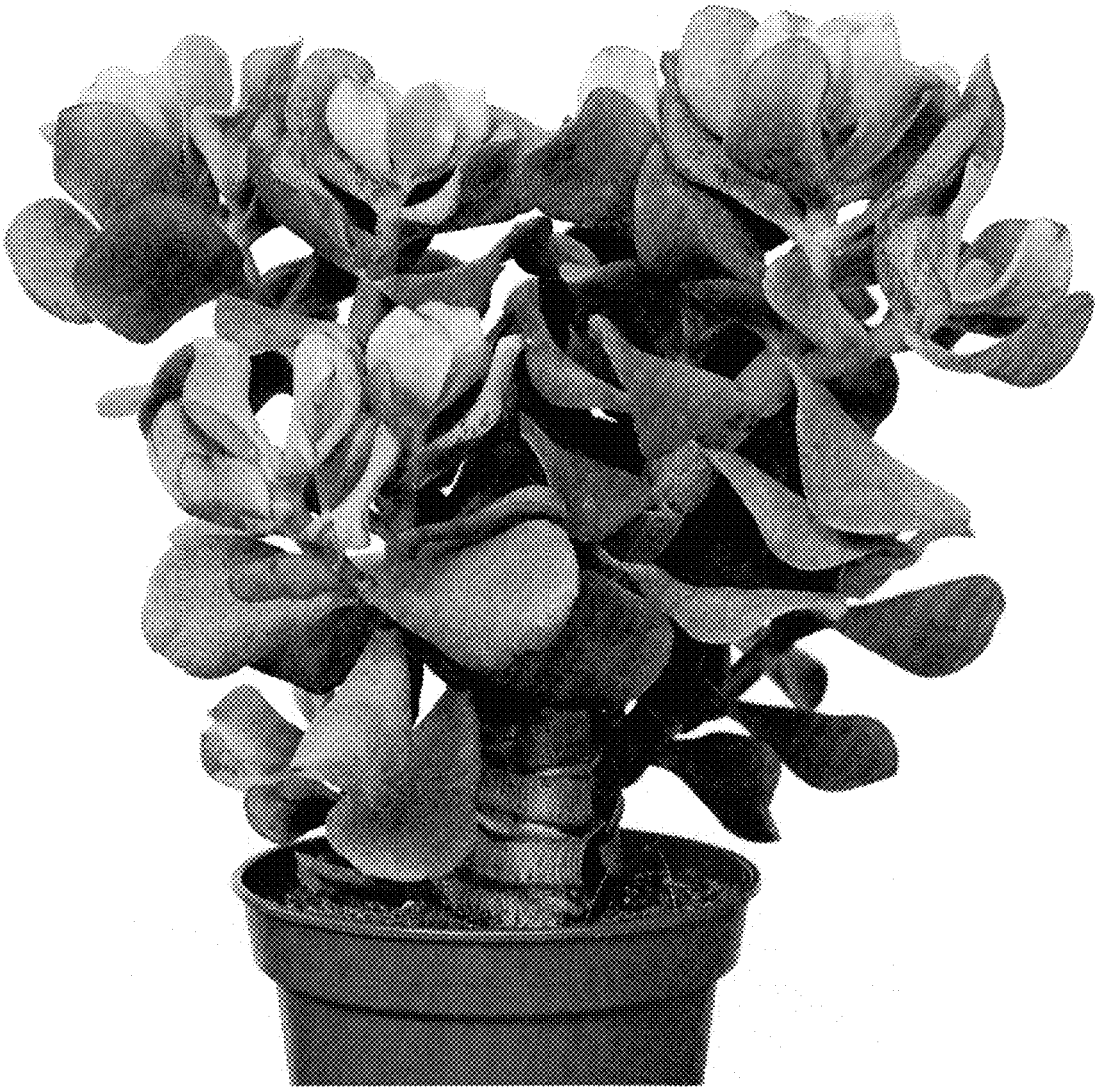
FIG. 1 illustrates, as nearly true as it is reasonably possible to make the same in color photographs of this type, an exemplary plant of 'OVWOODS05' grown in a commercial greenhouse in Heerhugowaard, The Netherlands. This plant is approximately 4 years old, shown planted in a 15 cm container.
Figure 2:
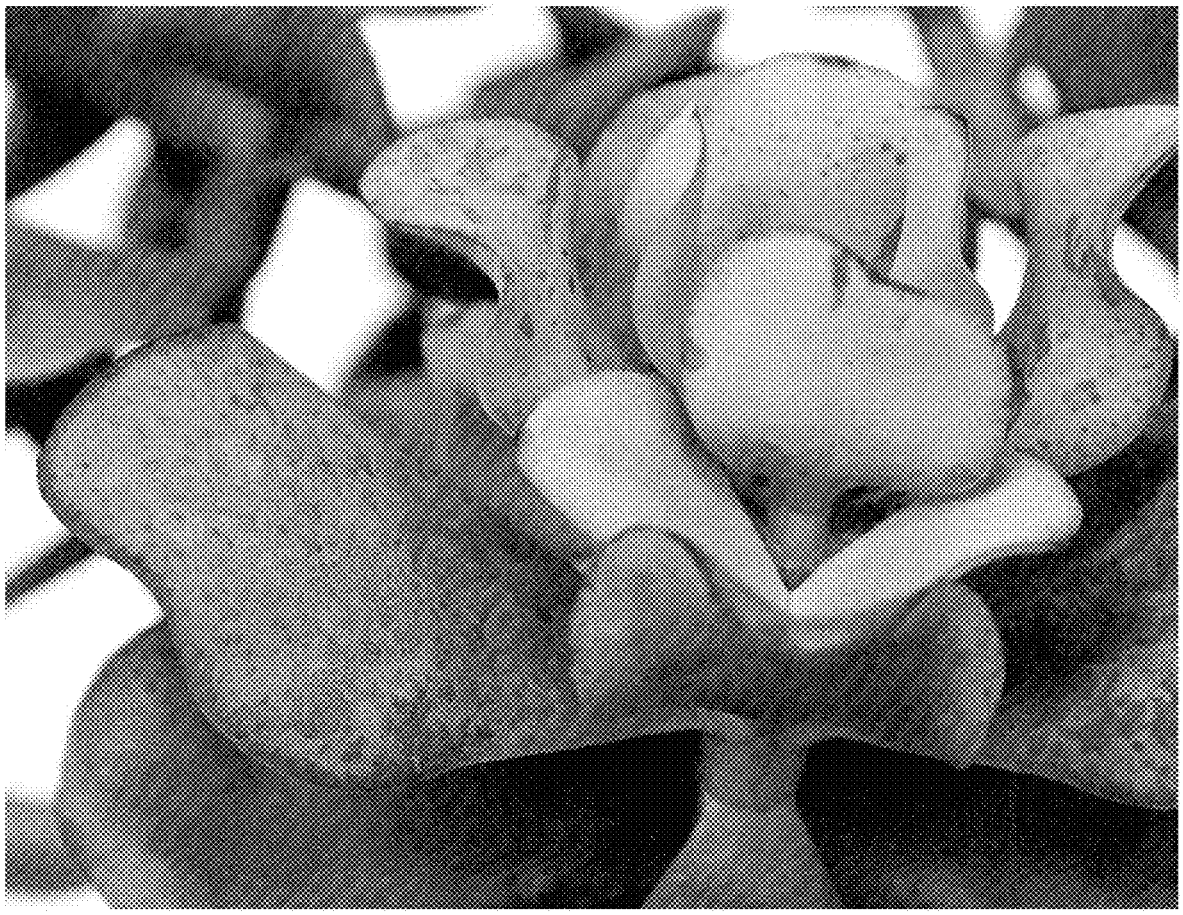
FIG. 2 illustrates, as nearly true as it is reasonably possible to make the same in color photographs of this type, the typical foliage of 'OVWOODS05'.

The following observations and measurements made in November of 2022 describe averages from a sample set of six specimens of 6-month-old 'OVWOODS05' plants grown in 13 cm nursery containers at commercial greenhouse in Bleiswijk, The Netherlands. The plants were grown in full sun to semi-shade. Plants were maintained with a standard fertility program for plants of this type and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'OVWOODS05' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'OVWOODS05' and comparisons with the parent and closest known commercial comparator are provided below.

Plant description:

*Growth habit.*—Broad spreading to upright perennial.

*Plant form.*—Irregular broad obovate to near flattened globular.

*Average height.*—26.2 cm from the soil level to the top of the foliar plane.

*Plant spread.*—Average of 35.6 cm.

*Plant vigor.*—Moderately vigorous.

*Propagation type.*—Stem cuttings.

*Time to initiate roots.*—Approximately 14 days to initiate roots at temperatures ranging from 15 to 20 degrees Celsius.

*Time to produce a rooted cutting.*—Approximately 6 weeks to produce a rooted cutting.

*Disease resistance.*—Neither resistance nor susceptibility to typical *Crassula* pests and diseases has been observed.

*Environmental tolerances.*—Adapt to, at least, USDA Zones 10 and 12 and temperatures as high as 40 degrees Celsius; low tolerance to rain; moderate to high tolerance to wind.

Root system:

*General.*—Moderately dense and freely branched rooting; roots are moderately fibrous.

*Distribution in the soil profile.*—Shallow to moderately deep.

*Diameter of roots.*—0.8 mm on average.

*Texture.*—Smooth and glabrous.

*Color.*—Greyed-orange, nearest to RHS 164A.

Stem:

*General branching habit.*—A main stem, freely branching with lateral branches. Pinching isn't required but will improve branching.

*Main stems.*—Quantity of main stems per plant — 1. Attitude — Upright. Cross-section — Rounded. Texture — Glabrous; glaucous. Luster — Matte. Strength — Strong. Color, juvenile — Yellow-green, nearest to RHS 144B. Color, mature — Green, nearest to in between RHS 137B and 137C. Color of the oldest wood — Nearest to a combination of greyed-green and grey-brown; RHS 194A, 194B, 199A, and 199B.

*Lateral branches.*—Quantity of lateral branches — 6. Length of lateral branches — Approximately 14.4 cm. Diameter of lateral branches — Approximately 1.0 cm. Internode length — Approximately 2.0 cm. Attitude — At an average angle of 60 degrees to the main stem. Cross-section — Rounded. Texture — Glabrous; glaucous. Luster — Matte. Strength — Strong. Color, juvenile — Yellow-green, nearest to RHS 144B. Color, mature — Green, nearest to in between RHS 137B and 137C. Color at inter-nodes — Green, nearest to in between RHS 137B and 137C.

Foliage:

*Phyllotaxy.*—Decussate.

*Division.*—Simple.

*Attachment.*—Sessile.

*Quantity.*—16 per lateral branch.

*Attitude.*—Upward.

*Lamina.*—Shape — Obovate. Aspect — Longitudinally convex; slightly to moderately curled upward, distally. Dimensions — 6.9 cm long and 4.2 cm wide. Thickness — Approximately 0.6 cm. Apex — Broad, bluntly acute to obtuse; occasionally shallow retuse. Base — Cuneate. Margin — Entire; coarsely, not undulated to lightly undulated. Pubescence, texture and luster of the adaxial surface — Glabrous, smooth, and matte; heavily glaucous. Pubescence, texture and luster of the abaxial surface — Glabrous, smooth, and matte; heavily glaucous. Color — Juvenile foliage, adaxial surface — Nearest to a mixture of green and yellow-green, RHS 138A and 146B; narrowly margined greyed-purple, nearest to RHS 183A. The epicuticular wax covering the leaf surface is greyed-green, nearest to a mixture of RHS 188A and 189B. Juvenile foliage, abaxial surface — Nearest to a mixture of green and yellow-green, RHS 138A and 146B yet nearest to RHS 146B; narrowly margined greyed-purple, nearest to RHS 183A. The epicuticular wax covering the leaf surface is greyed-green, nearest to RHS 189B. Mature foliage, adaxial surface — Green, nearest to RHS NN137A yet slightly darker; narrowly margined greyed-purple, nearest to RHS 184A. The epicuticular wax covering the leaf surface is greyed-green, nearest to RHS 189A. Mature foliage, abaxial surface — Green, nearest to RHS NN137B; narrowly margined greyed-purple, nearest to RHS 184A. The epicuticular wax covering the leaf surface is greyed-green, nearest to a mixture of RHS 189A and N189B. Venation — No veins are visible.

Inflorescence: No flowering has been observed to date.

Comparison with the parent plant: Plants of the new cultivar 'OVWOODS05' differs from the parent, an unnamed *Crassula* 'OVCRAS03' (Community Plant Variety Rights grant number 46259), in the following characteristics described in Table 1 below.

TABLE 1

| Characteristic | 'OVWOODS05' | 'OVCRAS03' |
|---|---|---|
| Plant size. | Larger than 'OVCRAS03'. | Smaller than 'OVWOODS05'. |
| Length and diameter of lateral branches. | Larger than 'OVCRAS03'. | Smaller than 'OVWOODS05'. |
| Foliage size. | Larger than 'OVCRAS03'. | Smaller than 'OVWOODS05'. |
| General coloration of the foliage. | Darker green by comparison to 'OVCRAS03' with a heavier covering of greyed-green epicuticular wax. | Lighter green by comparison to 'OVWOODS05' with a lighter covering of greyed-green epicuticular wax. |
| Foliage luster. | Matte. | Somewhat glossy. |

Comparison with the closest known comparator: Plants of the new cultivar 'OVWOODS05' differ from the most similar variety known to the inventor, *Crassula* 'Crasmada' (U.S. Plant Pat. No. 28,426), in the following characteristics described in Table 2 below.

TABLE 2

| Characteristic | 'OVWOODS05' | 'Crasmada' |
|---|---|---|
| Plant size. | Larger than 'Crasmada'. | Smaller than 'OVWOODS05'. |
| Length of lateral branches. | Longer than 'Crasmada'. | Shorter than 'OVWOODS05'. |
| Foliage size. | Larger than 'Crasmada'. | Smaller than 'OVWOODS05'. |
| Foliage apex. | Broad, bluntly acute to obtuse; occasionally shallow retuse. | Broad acute. |

That which is claimed is:

1. A new and distinct variety of *Crassula* plant named 'OVWOODS05', substantially as described and illustrated herein.

* * * * *